(12) United States Patent (10) Patent No.: US 8,313,638 B2
Marchal et al. (45) Date of Patent: Nov. 20, 2012

(54) METHOD FOR THE ELECTROCHEMICAL DETECTION OF TARGET NUCLEIC ACID SEQUENCES

(75) Inventors: Damien Marchal, Paris (FR); Benoît Limoges, Bretigny-sur-Orge (FR); Murielle Dequaire, Dijon (FR)

(73) Assignees: Universite Paris Diderot-Paris 7, Paris Cedex (FR); Universite de Bourgogne, Dijon Cedex (FR); Centre National de la Recherche Scientifique, Paris Cedex (FR)

( * ) Notice: Subject to any disclaimer, the term of this patent is extended or adjusted under 35 U.S.C. 154(b) by 867 days.

(21) Appl. No.: 12/280,826

(22) PCT Filed: Mar. 2, 2007

(86) PCT No.: PCT/FR2007/000373
§ 371 (c)(1),
(2), (4) Date: Sep. 23, 2008

(87) PCT Pub. No.: WO2007/099236
PCT Pub. Date: Sep. 7, 2007

(65) Prior Publication Data
US 2009/0065372 A1 Mar. 12, 2009

(30) Foreign Application Priority Data

Mar. 3, 2006 (FR) .................................... 06 01936
Jan. 10, 2007 (FR) .................................... 07 00157

(51) Int. Cl.
*G01N 27/49* (2006.01)
(52) U.S. Cl. .................... 205/793.5; 205/792; 435/6.12; 204/403.01

(58) Field of Classification Search .......... 204/400–435; 205/775–794.5; 600/345–348; 435/4–40.52; 422/68.1–98; 436/62–71, 500–548
See application file for complete search history.

(56) References Cited

U.S. PATENT DOCUMENTS 7,892,414 B1 * 2/2011 Sumner ........................ 205/778
2002/0081588 A1 * 6/2002 De Lumley-woodyear et al. .................................. 435/6
2002/0106683 A1 8/2002 Thorp et al.

FOREIGN PATENT DOCUMENTS
EP 1 500 933 1/2005
* cited by examiner

*Primary Examiner* — Kaj K Olsen
*Assistant Examiner* — Susan D Leong
(74) *Attorney, Agent, or Firm* — Ostrolenk Faber LLP

(57) ABSTRACT

The invention relates to a method and a collection for the electrochemical detection of target nucleic acid sequences. According to the method, a biological sample that may contain a nucleic acid is provided, said nucleic acid being capable of containing a target sequence, said biological sample being mixed with an oxidizing agent, said target sequence comprising at least one nucleotide base that can be oxidized by said oxidizing agent; complementary means capable of coupling with said target sequence are provided; according to the invention, said complementary means comprise activatable amplification means suitable for replicating said target sequence, said amplification means comprising at least nucleotides which include said nucleotide base, wherein said nucleotides are able to be consumed during replication so as to constitute replicated nucleic acids; and the presence of said target sequence is determined by applying an electric field to said sample and recording the decrease in the electric current.

19 Claims, 4 Drawing Sheets

METHOD FOR THE ELECTROCHEMICAL DETECTION OF TARGET NUCLEIC ACID SEQUENCES

CROSS REFERENCE TO RELATED APPLICATIONS

The present application is a 35 U.S.C. §371 National Phase conversion of PCT/FR2007/000373, filed Mar. 2, 2007, which claims benefit of French Application No. 06 01 936, filed Mar. 3, 2006, and French Application No. 07 00 157, filed Jan. 10, 2007, the disclosure of which is incorporated herein by reference. The PCT International Application was published in the French language.

The present invention relates to a method for the electrochemical detection of target nucleic acid sequences and to a detection collection for implementing said method.

Known methods already make it possible, by virtue of electrochemical detection, to identify the presence or absence of a target nucleic acid sequence of a given biological sample.

These methods make it possible in particular to detect, in a nucleic acid, a target sequence corresponding, for example, to a part of the genetic inheritance of a given virus.

According to the known techniques, once this nucleotide sequence has been identified, probes formed from oligonucleotides incorporating said sequence are prepared and then these probes are attached to a solid support. The probes include a given number of nucleotides having an oxidizable nucleotide base. The given biological sample is then brought into contact with the solid support onto which said probes are grafted, in such a way that, where appropriate, the nucleic acid containing the target sequences hybridizes with the probe. The hybridized nucleic acid is then reacted with a transition metal complex capable of oxidizing the bases of the nucleotides of the oligonucleotide probe, and the presence or absence of this hybridization, which occurs if the biological sample comprises a nucleic acid including said target sequence, is determined by applying a variable electric field to the sample and by measuring, in parallel, the electric current which circulates therein. The electric current then depends on the number of given bases capable of being oxidized. In fact, when a potential scan is carried out and, in parallel, the electric current which circulates in the sample is recorded, the response in terms of electric current is different depending on whether the probe is hybridized with the nucleic acid containing the target sequence or whether it is not. In any event, the electric current for oxidization of the base of the nucleotides of the hybridized probe has a higher value than that associated with the oxidation of the base of the nonhybridized nucleotides.

Reference may in particular be made to document US 2002/106 683, which describes such a method of detection.

However, such a method is relatively complex to implement, since it is in particular necessary to prepare oligonucleotide probes in order to graft them onto the solid support, this process being long and expensive.

Thus, a problem which arises and which the present invention aims to solve is that of providing a method which not only is easy to implement but, in addition, is more economical.

With the aim of solving this problem, and according to a first aspect, the present invention proposes a method for the electrochemical detection of target nucleic acid sequences, said method being of the type according to which: a biological sample that may contain at least one nucleic acid is provided, said nucleic acid being capable of containing a given target sequence, said biological sample being mixed with an oxidizing agent, said target sequence comprising a nucleotide base that can be oxidized by said oxidizing agent; complementary means capable of coupling with said given target sequence are provided; an electric field is applied to said sample, said electric field being capable of causing a reaction of said oxidizing agent with said nucleotide base, and an electric current which passes through said sample is measured in order to determine the presence of said target sequence; according to the invention, said complementary means comprise activatable amplification means suitable for replicating said target sequence, said amplification means comprising at least nucleotides of a type which includes said nucleotide base, wherein said nucleotides of said type are able to be consumed during replication so as to constitute replicated nucleic acids; and the presence of said given target sequence is determined if the electric current decreases when said amplification means are activated.

Thus, one feature of the invention lies in the implementation of a method for amplifying a nucleic acid and for simultaneously measuring an electric current, the measurement of this electric current attesting to or not attesting to the consumption of one of the elements of the amplification means during said amplification, and, specifically, of one of the free nucleotides. In this way, if the target nucleic acid sequence corresponds well to the activatable amplification means, this target sequence will be replicated during the amplification process, and the number of free nucleotides used as substrate during this replication, and the concentration of which is determined at the start, will decrease. Consequently, if the number of free nucleotides decreases to the benefit of the number of nucleotides incorporated into the nucleic acids synthesized during the amplification, the oxidizing agent will only be able to react with an increasingly limited amount of nucleotide bases corresponding to the free nucleotides, and consequently fewer electron transfers will occur, and the electric current finally measured will decrease. It will, however, be explained in greater detail in the detailed description which follows that the oxidizing agent may also oxidize the bases of the nucleotides incorporated into the nucleic acid initially present and into the nucleic acids synthesized by replication, but that, on the other hand, the electric current which results therefrom is weak compared with that which results from the oxidation of the bases of the free nucleotides.

According to a particularly advantageous embodiment of the invention, the nucleic acid on which it is sought to identify a target sequence is a single-stranded or double-stranded DNA or RNA molecule. Thus, the activatable amplification means comprise means suitable for hybridizing upstream of a target sequence and means for carrying out the replication of said sequence. The number of nucleic acids resulting from this replication increases exponentially over time, such that the number of free nucleotides exhibiting the oxidizable nucleotide base also decreases exponentially over time, and that, in parallel, the decrease in the current which passes through the sample is rapidly noticeable.

Advantageously, the nitrogenous base which is associated with the free nucleotides is a purine nucleotide base, for example guanine or a chemical analog of guanine, for example of the mercaptoguanine or oxoguanine type, and the oxidizing agent used is a ruthenium complex. The latter has a reduced form and an oxidized form, the latter irreversibly catalyzing the oxidization of guanine. When the electric field is applied to the mixture, the measured current which results therefrom depends substantially on the concentration of free nucleotides having the guanine residue, since, although the oxidizing agent also oxidizes the guanine of the nucleotides incorporated into the replicated nucleic acid, the oxidation kinetics and also the diffusion coefficient of the free nucleotides are much greater than that of said replicated nucleic acids.

In addition, since the number of nucleic acids resulting from the replication of said target sequences depends on time, the decrease in the current which passes through the sample thus also depends on time. Thus, if the starting sample has a high concentration of nucleic acid, and if these nucleic acids of the same type all have the target sequence, the consumption of nucleotides will be all the greater. Thus, the measurement of the variation in electric current will be all the more rapidly noticeable. On the other hand, if the concentration of nucleic acid is lower, a longer period of time will be necessary in order to observe the variation in current. As a result, said invention is applicable for a quantitative determination of the target sequence.

Thus, in practice, an electric field will be applied and the current which results therefrom will be measured, for example at time zero, and then regularly so as to be able to record the decrease in the electric current throughout the amplification process. Alternatively, the electric current may be recorded after a precise given time.

In fact, a priori, the concentration of free nucleotides having the guanine residue is at a maximum before the amplification has been started and, consequently, the electric current capable of passing through the sample is then also at a maximum. Subsequently, by comparing the measurement of the current in the course of or after the amplification, with the measurements which have been carried out during the amplification process, the difference can be assessed. If, in the course of these measurements, a significant decrease in the electric current is observed, this means that the free nucleotides having the guanine residue have been consumed, and therefore that the nucleic acid having the target sequence is indeed present in the sample. The additional verifications that are to be carried out before concluding that the target sequence is present will be explained in greater detail in the detailed description.

In addition, this electric current is measured after having applied the electric field for a relatively constant predetermined period of time for the same amplification. This is because, between the incident when the electric field is applied and the instant when the electric current which then passes through the sample is at a maximum, a transient phase sets in, during which the mobility of the ionized chemical species present in the sample will increase up to a maximum. Thus, in order to provide maximum sensitivity, it is preferable to measure the electric current when it is at a maximum, i.e. after a predetermined period of time, as will be explained in greater detail hereinafter. Be that as it may, the measurement of the electric current is carried out by means of known electrochemical techniques of the potential sweep voltammetry type, which may be linear, cyclic or pulse sweep voltammetry, or else of the potential step type, such as chronoamperometry.

In addition, and preferably, said electric field is applied between electrodes suitable for being bathed in said sample. For example, an electric field is applied between a metal oxide-based or carbon-based electrode or alternatively a noble metal-based electrode, and a reference electrode, both immersed in the sample, taking care to have a constant active surface of the electrodes for each current measurement of the same amplification so as to be certain that the variation in current is the result of the decrease in charge carriers and not of the variation in surface. An electrode made of a noble metal such as gold or platinum may, for example, be chosen.

According to another particularly advantageous embodiment of the invention, said oxidizing agent is confined to the surface of one of said electrodes, either by means of a gel, a membrane or a film applied to the electrode and which precisely traps the oxidizing agent; or by means of a polymer to which the oxidizing agent is coupled, the whole being adsorbed or grafted onto the surface of one of the electrodes.

According to another aspect, the present invention proposes a collection for the electrochemical detection of target nucleic acid sequences, said collection comprising: means for receiving a biological sample that may contain at least one nucleic acid, said nucleic acid being capable of containing a given target sequence, said biological sample being mixed with an oxidizing agent, said target sequence comprising a nucleotide base that can be oxidized by said oxidizing agent; complementary means capable of coupling with said given target sequence; means for applying an electric field to said sample, said electric field being capable of causing a reaction of said oxidizing agent with said nucleotide base, and means for measuring an electric current which passes through said sample in order to determine the presence of said target sequence; according to the invention, said complementary means comprise activatable amplification means suitable for replicating said target sequence, said amplification means comprising at least nucleotides of a type which includes said nucleotide base, wherein said nucleotides of said type are able to be consumed during replication so as to constitute replicated nucleic acids; and said measuring means give a decreasing electric current value when said amplification means are activated, if said nucleic acid contains said given target sequence.

Other particularities and advantages of the invention will emerge on reading the description given hereinafter of specific embodiments of the invention, given by way of nonlimiting indication, with reference to the attached drawings in which.

The method for the electrochemical detection of target nucleic acid sequences according to the invention aims to combine the implementation of a method for amplifying a nucleic acid and the implementation of an electrochemical method so as to be able to follow the decrease in a particular chemical species, reflecting the presence of said target nucleic acid sequence. The amplification method which will be described below is of the "PCR type", for: polymerase chain reaction. However, any other amplification method could be used with the same effectiveness. Mention will in particular be made of methods of the type "LCR" for: ligase chain reaction; "SDA" for strand displacement amplification; "RCA" for rolling circle amplification; "NASBA" for nucleic acid sequence based assay or amplification; or else "HDA" for helicase-dependent isothermal DNA amplification.

The principle of the "PCR"-type method consists in repeatedly using one of the properties of DNA polymerases for synthesizing, by replication using the two complementary strands making up the DNA and a pair of primers, two new strand copies of the two initial strands, the primers being small strands of nucleic acid of approximately 20 bases, capable of hybridizing specifically, by virtue of the base complementarity, to each of the two DNA strands to be replicated. Of course, the primers are chosen according to a target sequence to be revealed on a nucleic acid.

In addition to the DNA polymerases, which make it possible, after the primer has hybridized to a strand, to synthesize a complementary strand from this primer, nucleotides are also provided, and in particular the four nucleotides dGTP, dATP, dTTP and dCTP constituting DNA (respectively deoxyguanine triphosphate, deoxyadenosine triphosphate, deoxytyrosine triphosphate and deoxycytosine triphosphate), that the DNA polymerase assembles so as to form a replicated complementary strand.

Moreover, the reaction medium into which are introduced: the test sample that may contain the target nucleic acid sequence, the DNA polymerase, the primers and the four types of nucleotides and which form a reaction mixture, is of course liquid and buffered. In addition, and according to the method, this reaction mixture will be alternately subjected to variations in temperature, corresponding to various phases, of denaturation, of hybridization, and of extension of the nucleic acid, over the course of the same cycle. Conventionally, the reaction mixture may successively undergo about thirty cycles.

Moreover, and this is a subject of the invention, the amplification method, the principle of which has been described above, will be coupled to electrochemical means for revealing, where appropriate, the disappearance of the nucleotides of one of the four types, over the course of the amplification cycles, said nucleotides of said one of the four types being incorporated into the complementary DNA strands through the action of the DNA polymerase.

Figure 1:
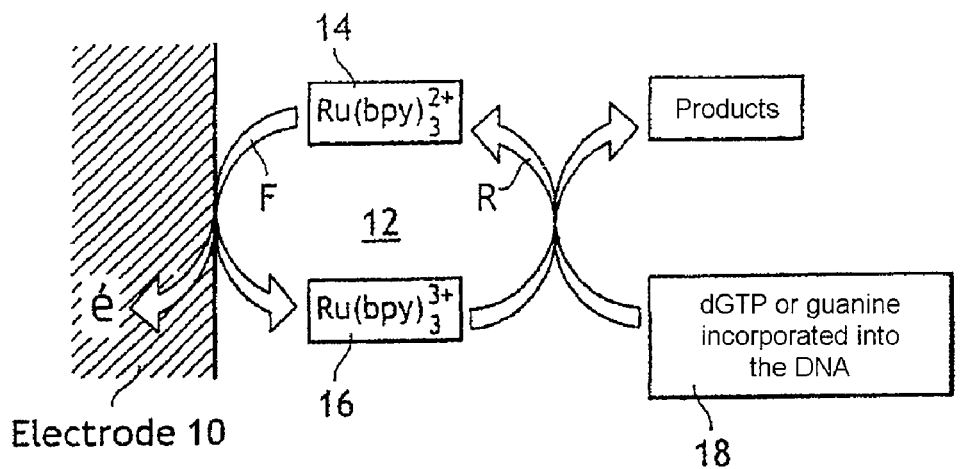
FIG. 1 is a reaction scheme showing schematically chemical and electrochemical reactions occurring during the implementation of the method according to the invention.

To do this, an oxidizing agent, and in particular a ruthenium complex, for example tris(2,2'-bipyridyl)ruthenium(II), which is capable, in its oxidized form, to in turn oxidize the guanine of the nucleotides having the guanine residue: dGTP, is used. Of course, any other oxidizing agent capable of oxidizing guanine may be used; mention will, for example, be made of $IrCl_6^{4-}$. As illustrated in FIG. 1, in which is represented an electrode 10 immersed in an aqueous reaction medium 12, the oxidizing agent being incorporated into the abovementioned reaction mixture, when an electric field is applied to this mixture, the oxidizing agent first of all changes from its reduced form 14 to its oxidized form 16 according to the arrow F, giving up an electron to the electrode 10. Moreover, in its oxidized form 16, the oxidizing agent is capable of in turn oxidizing a guanine of a nucleotide 18 having precisely a guanine residue, and which is either free or is inserted into a nucleic acid. In oxidizing this guanine, the oxidizing agent is simultaneously reduced according to the arrow R, whereas the guanine definitively oxidized is no longer involved in the reaction. The current measured at the electrode, i.e. the electron flow, is essentially due to the current from oxidation of the free nucleotides having a guanine residue and to a minute extent to the nucleotides inserted in a DNA strand. One explanation may be provided by the difference in diffusion coefficient, but also the difference in guanine oxidation kinetics between a nucleotide having a free guanine residue and a nucleotide having a guanine residue incorporated into a nucleic acid.

Consequently, if the nucleotides which include guanine are consumed during the amplification cycles to the same extent as the other nucleotides, in order to synthesize replicated nucleic acids which statistically include virtually the same number of nucleotides of each of the abovementioned four types, the electron flow and, consequently, the current measured at the electrode will itself also decrease accordingly.

With the aim of illustrating the method in accordance with the invention, an exemplary embodiment will be described hereinafter.

Figure 2:
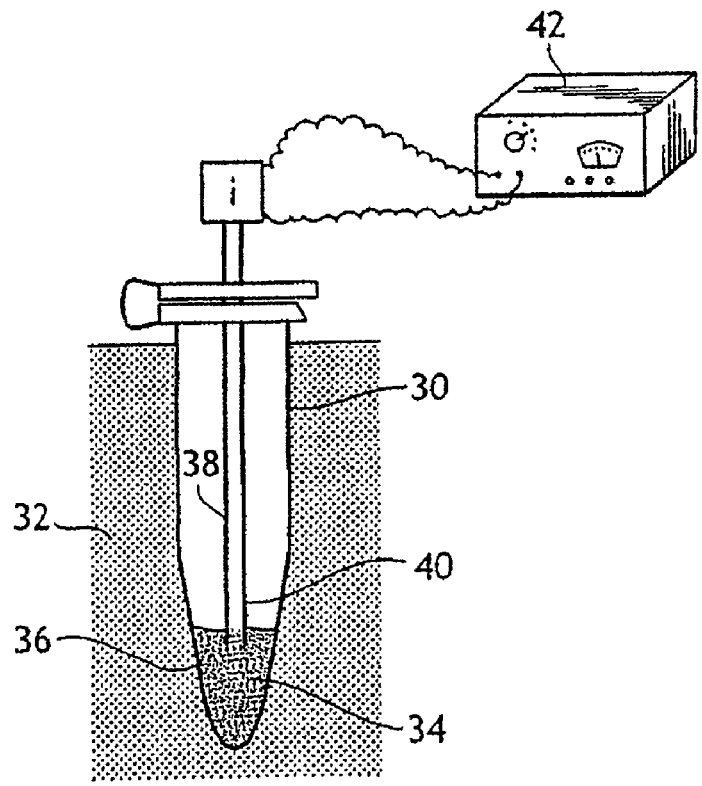
FIG. 2 is a schematic view showing a first collection for implementing the method in accordance with the invention according to a first embodiment.

FIG. 2 illustrates, according to a first embodiment, a tube 30 that can be installed in a thermocycler 32 which itself will make it possible to bring the tube 30 to predetermined temperatures, representative of the various steps of the amplification according to the "PCR"-type method. Conventionally, in a first step of a cycle, the tube is heated for a few seconds at 94° C. so as to cause denaturation of the nucleic acid, and in this case of the DNA. Next, in a second step of approximately one minute, the temperature is rapidly decreased to 58° C. so as to bring about hybridization of the primers. Then, the tube is subsequently brought to a temperature of 72° C. for one minute also, so as to activate the DNA polymerase in order to bring about extension of the complementary strands. Subsequently, a new cycle is begun.

The reaction mixture 34 is housed in the pellet 36 of the tube 30 and two electrodes 38, 40 introduced into the tube 30 are immersed in the reaction mixture 34. One of the electrodes, 38, is a carbon electrode, for example, whereas the other electrode 40 is the reference electrode. These electrodes 38, 40 are respectively connected to a potentiostat 42 which makes it possible to vary an electric potential according to a given profile, between the two electrodes, and to record, in parallel, the electric current which passes through them.

Figure 3:
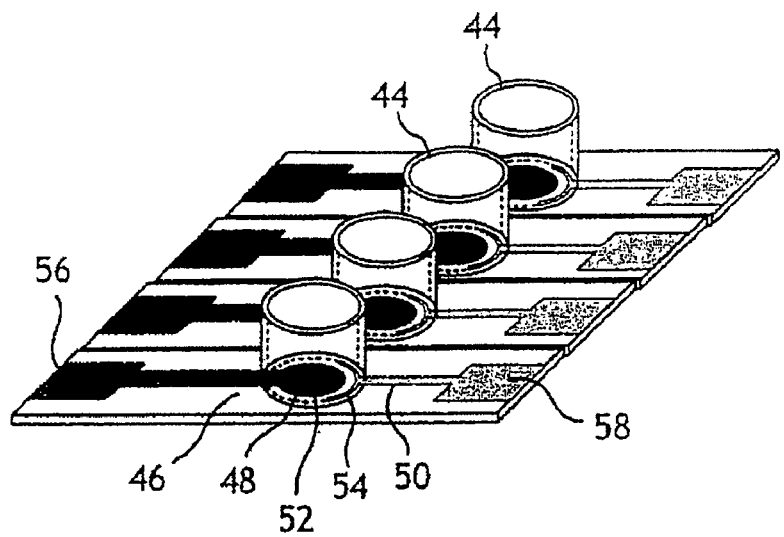
FIG. 3 is a schematic view showing an element of a device for implementing the method in accordance with the invention and according to a second embodiment.

According to a second embodiment, the essential elements of which have been reproduced in FIG. 3, the amplification method is in all respects identical to the abovementioned method. However, the detection is no longer carried out during the amplification, but at the end of the latter. In this case, no electrode is directly introduced into the tube 30, but the reaction mixture 34 is itself introduced into one or more microcuvettes 44 illustrated in FIG. 3. These microcuvettes 44 are sealed in a leaktight manner on a plate of "integrated circuit" type 46, on which electrodes 48, 50 have been screen printed. These electrodes 48, 50 have, respectively, an active end 52, 54 located in the bottom of the microcuvettes 44 and they extend out to connecting ends 56, 58, respectively. In the same manner as in the first embodiment mentioned above, the connecting ends 56, 58 are able to be connected to a potentiostat in order to apply an electric field to the reaction mixture located in the microcuvette 44.

It will be noted that these microcuvettes 44 are also suitable for amplification methods of the "NASBA", "RCA" or "HDA" type mentioned above.

APPLICATION EXAMPLE 1

An example of application of said method for detecting the presence of the cytomegalovirus (CMV) in a biological sample will be described in detail hereinafter. The genome of this virus has a well-identified sequence of 406 base pairs and the two commercial primers AC1 and AC2, which allow the specific amplification of this sequence, are used (references 60-003 and 60-004 from the company Argene). The total volume of the reaction mixture is equal to 50 μl and it contains the two primers at a concentration of 0.8 μmol/l, the nucleotides of the four types at a concentration of 100 μmol/l, the polymerase at a concentration of 0.02 unit per μl, a ruthenium complex concentration of 20 μmol/l, and a one-tenth dilution of 10× buffer. Of course, the reaction mixture contains a biological sample and, in the case in point, a cell extract incorporating the cytomegalovirus.

The electrochemical measurement is carried out using the potentiostat 42 through the application of a voltammetric technique which consists in applying a potential variation between the two electrodes 38, 40 or 52, 54, starting, for example, from an initial potential of 0.5 V relative to a calomel electrode, up to a final potential of 1.3 V (relative to the same calomel electrode), for a sweep rate that may be between 0.01 and 100 V per second. In parallel, the resulting electric current is recorded during the potential sweep.

Figure 4:
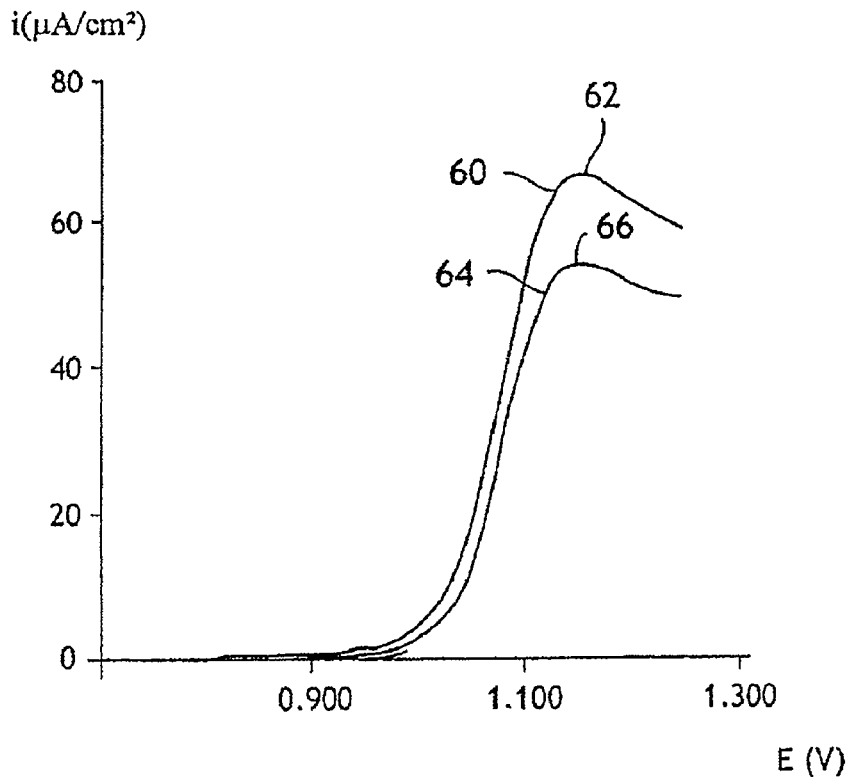
FIG. 4 is a graph representing curves of change in electric current as a function of an applied potential and illustrating the method in accordance with the invention.

Reference will be made to FIG. 4, in which are shown two voltammetric curves recorded at a rate of 0.1 V·s$^{-1}$ by the potentiostat as a function of the potential difference applied between the abovementioned electrodes, and represented herein as current density. A first curve 60 represents the change in the electric current measured at the second amplification cycle according to the abovementioned experiment. The biological sample initially contained 100 000 copies of the target sequence. This curve reaches a first extreme 62 of approximately 68 μA per cm$^2$. A second curve 64 represents the change in the electric current measured at the thirtieth cycle according to the abovementioned experiment. This curve reaches a first extreme 66 of approximately 56 μA per cm$^2$. This extreme 66 is located approximately 12 μA per cm$^2$ below the first extreme 62.

Moreover, it was clearly verified beforehand that the two steps of the abovementioned operating scheme, applied to a biological sample containing no cytomegalovirus, with the abovementioned amplification means, resulted in two substantially identical curves being obtained. Consequently, when the virus is not present in the biological sample, the amplification does not take place.

Thus, it is very clearly apparent, by comparing the two curves 60, 64, that the intensity of the electric current decreased after 30 amplification cycles relative to its initial value before amplification. Consequently, it is clearly apparent that the presence of the cytomegalovirus in the nucleic acid of the biological sample was recognized by the corresponding primers AC1 and AC2, and that the extension of the complementary strands clearly occurred, with the nucleotides, and in particular the nucleotides of the dGTP type having the guanine residue, being consumed, since it is the base of only this nucleotide that the oxidizing agent, the ruthenium complex, is capable of oxidizing. Now, the measurement of the electric current is essentially the result of the measurement of the electron flow corresponding to the reduction of the ruthenium complex and, in parallel, to the oxidation of the nucleotides which include the dGTP guanine. Thus, when the latter nucleotides partially disappear, since they are integrated into the complementary nucleic acid strands, their amount in the free state decreases and, consequently, the oxidation current which results therefrom also decreases.

Figure 5:
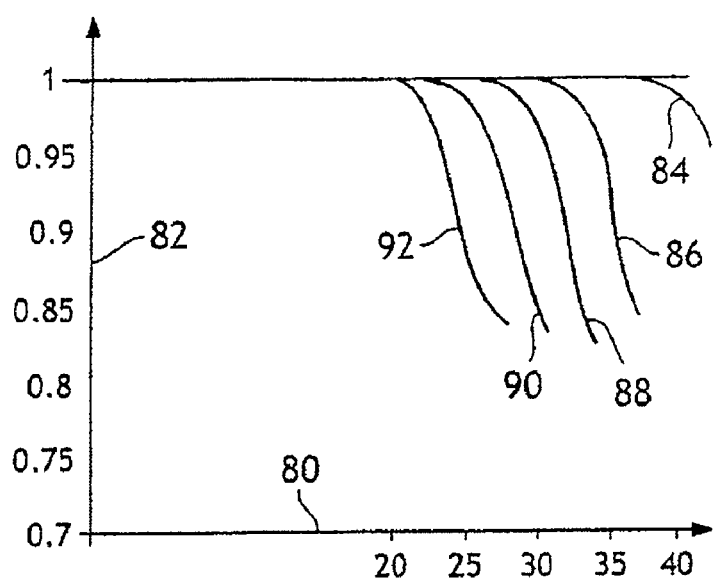
FIG. 5 is a graph showing the decrease in an electric current as a function of an amplification process.

Moreover, reference will at present be made to the graph illustrated in FIG. 5, to describe the principle of the quantification of a target sequence of a nucleic acid in a given sample.

Along the x-axis 80 of the graph are the numbers of replication cycles and along the y-axis 82 are reported the normalized values of the currents recorded at each cycle at a given potential according to the embodiment illustrated in FIG. 2. These normalized current values correspond to the current measurements divided by the measurement of the current carried out before the start of the amplification.

The five curves represented, 84, 86, 88, 90, 92, represent the curves plotted by starting from a biological sample comprising, respectively, zero copy of the CMV target sequence, 84; 1000 copies of said target sequence, 86; 10 000 copies of said target sequence, 88; 100 000 copies of said target sequence, 90; and 1 000 000 copies of said target sequence, 92.

Thus, it is noted that, the greater the content of nucleic acids which incorporate the target sequence, in the biological sample, the more rapidly the electric current which passes through the sample decreases as a function of the number of cycles. This is because the greater the content of nucleic acids which incorporate the target sequence, in the sample initially, the more replication will consume nucleotides of the dGTP type and, consequently, the earlier the electric current will drop as a function of the number of cycles. In this way, it is understood that a measurement of the amount of nucleic acids which incorporate the target sequence is possible by determining the number of cycles starting from which the amount of current which passes through the sample dips. In addition, this FIG. 5 also shows that the presence of the target sequence is detectable even if only 1000 copies of said target sequence are initially present in the sample.

Thus therefore, the method according to the invention applied to a biological sample that may contain an identified virus makes it possible not only, by virtue of the implementation of an amplification method and of an electrochemical measurement, to reveal the presence or absence of said virus, but also to quantify it. Consequently, in comparison with the methods used according to the prior art, for which the preparation of the material for identification is complex, according to the present invention, it is only necessary to carry out a conventional amplification method and then, during the amplification, to subject the biological sample to an electric field and to measure the current which results therefrom. This method uses an oxidizing agent which is in no way used in the conventional amplification methods, for revealing the disappearance of a species, in the case in point a type of nucleotide having the guanine residue or a compound having the same biological role as guanine. In addition, the choice of the oxidizing agent will depend on the nature of the nucleotide type whose disappearance it is desired to measure.

The exemplary embodiment above concerns a double-stranded nucleic acid, i.e. a DNA molecule. However, it can absolutely be applied to a single-stranded nucleic acid of RNA or DNA type, in return for the use of suitable amplification means. In the two cases, the amplification of these nucleic acids leads to the consumption of nucleotides which include guanine and, consequently, a decrease in this species in the medium as the amplification process occurs.

Thus therefore, whatever the embodiment of the method which is the subject of the invention, either the first method described above in support of FIG. 2, or the second method described with reference to FIG. 3, the moment from which the value of the electric current falls significantly is evaluated by carrying out measurements over the course of the amplification process. This makes it possible not only to reveal the presence of the target DNA sequence, but also to work back indirectly to the initial concentration of nucleic acid incorporating the target sequence to be detected. This is because, the higher the number of initial copies of nucleic acid incorporating the target sequence, the earlier the electric current will decrease and, conversely, the lower the number of copies, the later the drop in current will be observed.

Figure 6:
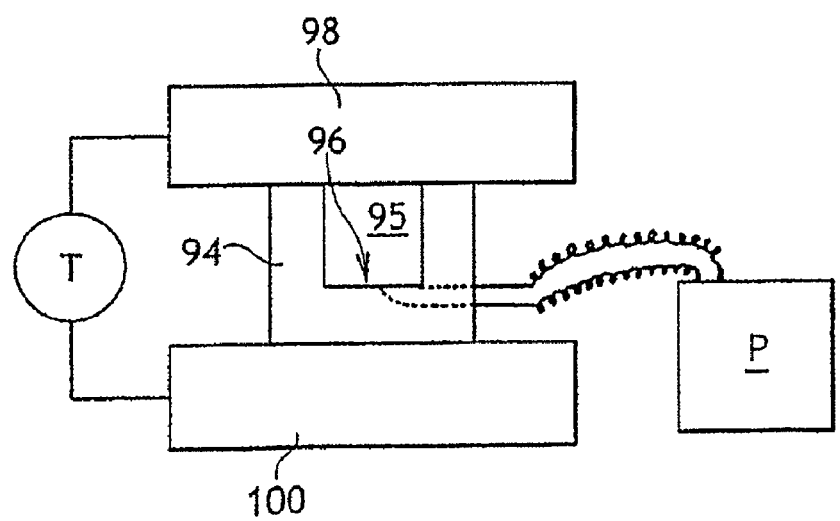
FIG. 6 is a schematic view of a second collection for implementing the method in accordance with the invention.

Moreover, and according to another aspect illustrated in FIG. 6, the present invention also relates to a collection especially suitable for the electrochemical detection of target nucleic acid sequences. This collection comprises at least one microcuvette 94 as represented in FIG. 3, for receiving a biological sample 95, but in this case equipped with a thermal insulation. This microcuvette 94 has screen-printed electrodes 96 in the bottom, which are connected to a potentiostat P. Moreover, the microcuvette 94 is placed between two Peltier-effect modules 98, 100 connected by a generator suitable for adjusting the temperature inside the microcuvette 94. In this way, the biological sample 95 is able to be brought to temperatures ranging up to 94° C. and according to abrupt variations, just like the abovementioned method of PCR type. Furthermore, activatable amplification material, and in particular nucleotides having an oxidizable nucleotide base, are added to the biological sample.

Thus, the collection illustrated in FIG. 6, which can be computer-controlled, is suitable for automatically providing the information that the target sequence sought is indeed contained in the sample placed in the microcuvette 94, and, if this is so, the concentration of nucleic acid comprising the target sequence.

The computer is therefore loaded with a computer program capable of simultaneously operating the replication means, i.e. the Peltier-effect modules 98, 100, according to predefined cycles, and the potentiostat between the cycles, so as to measure the amount of current passing through the sample 95 for given potential values.

In addition, when the amplification means are used, the surface condition of said electrode is modified. Moreover, as the amplification cycles take place, the solvent of the reaction mixture, in the case in point water, is liable to evaporate given the temperatures applied. Any evaporation of the solvent, by nature, brings about an increase in the concentration of the solutes.

Consequently, the measurement of the current which is proportional to the concentration of nucleotide base consumed might not be entirely correlated with the amount of nucleic acid amplified.

Thus, an underlying problem which then arises is that of being able to overcome both disturbances in the electrode and the evaporation of the solvent.

To do this, and according to yet another particularly advantageous embodiment of the invention, the detection method also comprises the following steps: a redox compound is provided, which is capable of reacting at a shifted electric field value different from the electric field value at which said oxidizing agent and said nucleotide base react; the value of the redox electric current at said shifted electric field value is measured; and the presence of said given target sequence is determined if the difference in electric current between the redox electric current and said electric current of reaction of said oxidizing agent and of said nucleotide base decreases when said amplification means are activated.

Thus, by choosing a redox compound, or internal standard, for example a ferrocene, a viologen or else an osmium complex, the oxidation potential of which is shifted relative to the oxidation potential of said oxidizing agent and of said nucleotide base, for example of 800 mV, the oxidation of the redox compound does not disturb the measurement of the oxidation current for the oxidizing agent and the base. In addition, this oxidizing agent does not interfere with the activatable amplification means.

Figure 7:
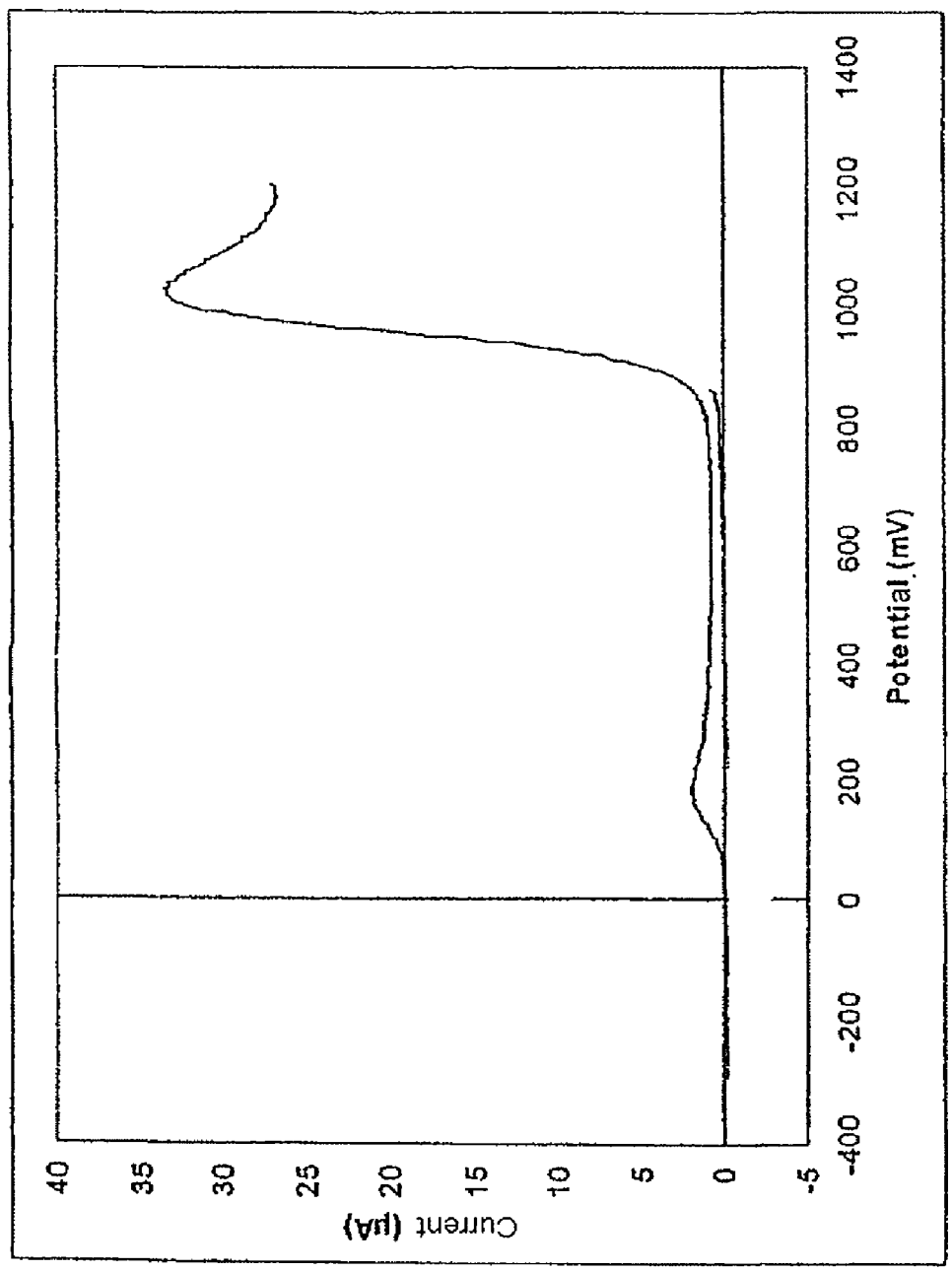
FIG. 7 is a graph showing a voltammetric curve.

According to a first embodiment in accordance with this other embodiment, for which reference may be made to FIG. 7, the normalization of the measurement of the electric current is carried out for a single sample during the same experiment.

Thus, a sample is used in a reaction mixture identical to that of the abovementioned application example, except that, in addition, ferrocene methanol is incorporated therein at a concentration of 50 µM and that a potential variation is applied between the two electrodes, starting at 50 mV and ending at 1300 mV. The voltammetric curve reported in FIG. 7 is thus obtained for the first amplification cycle.

This curve no longer has a single extreme, but two. A first extreme 210 is located at around 1100 mV relative to the saturated calomel electrode, and corresponds to the extremes of the curves illustrated in FIG. 4, and a second extreme 220 is located at around 200 mV and corresponds to the oxidation of the ferrocene methanol. The first extreme results from the oxidation of the oxidizing agent, the ruthenium complex, and the corresponding current measurement is approximately 32 µA, while the second, which results from the oxidation of the redox compound, is approximately 2 µA.

After the potential sweep between 50 mV and 1300 mV and the simultaneous recording of the intensity currents, the current corresponding to the first extreme 210 is normalized by dividing its value, in the example illustrated in FIG. 7: 32 µA, by the value of the current corresponding to the second extreme 220, which is 2 µA, and 16 is obtained.

Next, the same process is carried out for all the amplification cycles of said experiment. Thus, the measurement of the variation of the difference in the intensity values of the two extremes 210, 220 results only from the decrease in the concentration of nucleotide base, in the case in point the dGTPs, and makes it possible to overcome the experimental conditions.

Consequently, and according to a second embodiment, the process is carried out identically for a series of samples respectively introduced into a series of microcuvettes of the type of those illustrated in FIG. 3, so as to perform a series of experiments. These biological samples advantageously come from the same source, and here it is a question of confirming the presence of the given target sequence. Thus, by normalizing the intensity values corresponding to the oxidation of the oxidizing agent respectively for each of the experiments, they are then comparable to one another since they are independent of the variations in the volume and in the surface condition of the electrodes.

Thus, according to this other embodiment of the invention, the detection of the real consumption of nucleotides is refined, thereby making it possible to conclude that a target sequence is present after a small number of amplification cycles. Consequently, the time required to establish the diagnosis is reduced.

In addition, and as illustrated by the second embodiment mentioned above, measurements can be compared irrespective of the operating conditions.

APPLICATION EXAMPLE 2

In addition, the detection method according to the invention is not only applicable to viruses, but also to bacteria. Thus, it was used for detecting the presence of bacteria, and in particular *Achromobacter xylosoxidans*, mobile genetic elements of which, and more specifically the integrons, play a fundamental role in the acquisition of antibiotic-resistance genes.

Thus, three DNA fragments characteristic of this bacterial strain were identified and amplified by PCR-type methods. The implementation of the method according to the invention made it possible to detect the presence of the abovementioned bacterium by identifying a first gene "veb-1" having approximately 900 base pairs. This gene encodes a beta-lactamase which confers a high level of resistance to various antibiotics, and in particular amoxicillin and ticarcillin. The activatable amplification means comprise the four nucleotides, DNA polymerase and a pair of primers "VEB-F and VEB-R" specific for the gene, and they were incorporated into a biological sample containing said bacterium.

A voltamogram similar to that which is represented in FIG. 4 is thus observed. According to the experimental conditions, a first curve corresponding to a measurement of the electric current before having started the amplification shows an extreme of approximately 6 µA for a potential value of approximately 1.075 V. A second curve produced after amplification shows an extreme decreased by approximately 1 µA. Consequently, the decrease in the electric current results from the consumption of nucleotides during the amplification and, consequently, from the effective presence of the "veb-1" gene.

A second fragment, of 100 base pairs, of the "int I" gene, which are characteristic of the abovementioned bacterium, was identified and detected in the same manner.

A third fragment of 2500 base pairs, characteristic of said bacterium, could also be detected in a similar manner. The nucleotide sequence of this third fragment corresponds to a variable region of the integron containing all the cassettes, including the "veb-1" gene.

Thus, the method which is the subject of the invention can be applied to amplifications of fragments of genetic material of different sizes in different protocols and with different activatable amplification means or biological kits.

What is claimed is:

1. A method for the electrochemical detection of target nucleic acid sequences, said method comprising:
   providing a biological sample that may contain at least one nucleic acid, said nucleic acid being capable of containing a given target sequence, said biological sample being mixed with an oxidizing agent and activatable amplification composition, said activatable amplification composition comprising at least one nucleotide base that can be oxidized by said oxidizing agent;
   providing complementary composition capable of selectively coupling with said given target sequence;
   applying an electric field to said sample, said electric field being capable of causing a reaction of said oxidizing agent with said at least one nucleotide base, and an electric current which passes through said sample is measured;
wherein said activatable amplification composition is suitable for replicating said target sequence, said activatable amplification composition comprising at least nucleotides which include said at least one nucleotide base, wherein said nucleotides are able to be consumed during replication so as to constitute replicated nucleic acids;
and in that it comprises, in order, the following steps:
   a) mixing said biological sample and said oxidizing agent with said activatable amplification composition and said complementary composition;
   b) activating said activatable amplification composition in a plurality of cycles to consume at least a portion of the at least one nucleotide base if the target sequence is contained in the biological sample;
   c) applying said electric field to oxidize an unconsumed portion of the at least one nucleotide base; and
   d) determining the presence of said given target sequence based on a decrease in the electric current decreases after the plurality of cycles of activation of said activatable amplification composition.

2. The detection method as claimed in claim 1, wherein said nucleic acid comprises a DNA or RNA molecule.

3. The detection method as claimed in claim 1, wherein said at least one nucleotide base comprises a purine nitrogenous base.

4. The detection method as claimed in claim 3, wherein said at least one nucleotide base comprises guanine or a chemical analog of guanine.

5. The detection method as claimed in claim 1, wherein said oxidizing agent comprises a ruthenium complex.

6. The detection method as claimed in claim 1, wherein said target sequences are replicated successively over the plurality of cycles, and said electric current is measured by applying said electric field after different cycles of the plurality of cycles.

7. The detection method as claimed in claim 1, wherein said target sequence is replicated according to amplification cycles, and in that said current is measured after a predetermined number of cycles.

8. The detection method as claimed in claim 1, wherein said electric field is applied between electrodes suitable for being bathed in said sample.

9. The detection method as claimed in claim 8, wherein one of said electrodes comprises a metal oxide-based electrode.

10. The detection method as claimed in claim 8, wherein one of said electrodes comprises a noble metal-based electrode.

11. The detection method as claimed in claim 8, wherein one of said electrodes comprises a carbon electrode.

12. The detection method as claimed in claim 8, wherein said oxidizing agent is confined at the surface of one of said electrodes.

13. The detection method as claimed in claim 1, further comprising:
   providing a redox compound, capable of reacting at a shifted electric field value different from an electric field value at which said oxidizing agent and said at least one nucleotide base react; and
   measuring the value of the redox electric current at said shifted electric field value;
   wherein the presence of said given target sequence is determined based on whether a difference in electric current between the redox electric current and said electric current of reaction of said oxidizing agent and of said nucleotide base decreases when said amplification composition is activated.

14. A method for the electrochemical detection of target nucleic acid sequences, comprising:
   receiving a biological sample that may contain at least one nucleic acid, said nucleic acid being capable of containing a given target sequence, said biological sample being mixed with an oxidizing agent and an activatable amplification composition, said activatable amplification composition comprising at least one nucleotide base that can be oxidized by said oxidizing agent;
   selectively coupling a complementary composition with said given target sequence and cyclically activating said activatable amplification composition in a presence of said oxidizing agent to selectively amplify the given target sequence and consume a corresponding portion of the at least one nucleotide base;
   applying an electric field to said sample in conjunction with different cycles of activation of the activatable amplification composition, said electric field being adapted to cause a reaction of said oxidizing agent with an unconsumed portion of said at least one nucleotide base, and measuring a change in an electric current which passes through said sample in order to determine the presence of said target sequence.

15. A method for detection of a target nucleic acid sample, comprising:

obtaining a biological sample;

adding a polymerase chain reaction primer, nucleotides, and a deoxyribonucleic acid polymerase to the biological sample, along with at least one oxidizing agent to form a reaction mixture;

amplifying a target sequence corresponding to the polymerase chain reaction primer in the biological mixture containing the oxidizing agent in a plurality of amplification cycles, while consuming at least a portion of the nucleotides;

applying an electric field while measuring an electrical current after at least two different amplification cycles, to oxidize with the oxidizing agent an unconsumed portion of at least one type of nucleotide in the reaction mixture; and determining a concentration or amount of the at least one type of nucleotide based on the measured electrical current, wherein a reduction in the measured electric current, corresponding to a consumption of the unconsumed portion of the at least one type of nucleotide, is selectively indicative of a presence of the target sequence in the biological sample.

16. The method for detection of a target nucleic acid sample according to claim 15, wherein said at least one nucleotide comprises guanine or a chemical analog of guanine, and said oxidizing agent comprises a ruthenium complex.

17. The method for detection of a target nucleic acid sample according to claim 15, wherein the electric field is applied to a solution containing the reaction mixture through at least one electrode, and said oxidizing agent is confined at a surface of said at least one electrode.

18. The method for detection of a target nucleic acid sample according to claim 15, further comprising standardizing a measurement by providing a redox compound in the reaction mixture which undergoes a redox reaction at a shifted electric field value, different from an electric field value at which said oxidizing agent and said at least one nucleotide react, and measuring the both value of the electric current at said shifted electric field value and a value of the electrical current at an electric field value where the oxidizing agent and the at least one nucleotide react, at different times over the plurality of amplifications cycles.

19. The method for detection of a target nucleic acid sample according to claim 15, wherein the reaction mixture is not supplemented with reactants over the plurality of amplification cycles.

* * * * *